United States Patent [19]

Baumann et al.

[11] Patent Number: 5,352,671
[45] Date of Patent: Oct. 4, 1994

[54] HETEROATOMS-CONTAINING TRICYCLIC COMPOUNDS

[75] Inventors: Karl Baumann; Gerhart Emmer, both of Vienna, Austria

[73] Assignee: Sandoz Ltd., Basel, Switzerland

[21] Appl. No.: 697,864

[22] Filed: May 9, 1991

Related U.S. Application Data

[63] Continuation-in-part of Ser. No. 609,280, Nov. 5, 1990, abandoned.

[30] Foreign Application Priority Data

| Nov. 9, 1989 | [DE] | Fed. Rep. of Germany | 3937336 |
| Nov. 16, 1989 | [DE] | Fed. Rep. of Germany | 3938132 |
| Dec. 23, 1989 | [DE] | Fed. Rep. of Germany | 3942831 |
| Dec. 23, 1989 | [DE] | Fed. Rep. of Germany | 3942833 |
| Mar. 5, 1990 | [DE] | Fed. Rep. of Germany | 4006819 |

[51] Int. Cl.$^5$ .......... A61K 31/695; A61K 31/395; C07D 498/16
[52] U.S. Cl. .......... 514/63; 514/321; 514/291; 540/452; 540/456
[58] Field of Search .......... 540/456; 546/452; 514/63, 321

[56] References Cited

U.S. PATENT DOCUMENTS

| 5,143,918 | 9/1992 | Bochis et al. | 514/291 |
| 5,162,334 | 11/1992 | Goulet et al. | 340/452 |
| 5,189,842 | 2/1993 | Goulet et al. | 540/456 |
| 5,208,228 | 5/1993 | Ok et al. | 540/456 |

FOREIGN PATENT DOCUMENTS

| 0227355 | 7/1987 | European Pat. Off. | 514/456 |
| 0353678 | 2/1990 | European Pat. Off. | 514/63 |
| 8905304 | 6/1989 | World Int. Prop. O. | 540/456 |

OTHER PUBLICATIONS

J. Am. Chem. Soc. 1987, 109, 5031–5033, Tenaka, et al.

*Primary Examiner*—Robert T. Bond
*Attorney, Agent, or Firm*—Robert S. Honor; Melvyn M. Kassenoff; Thomas O. McGovern

[57] ABSTRACT

The invention concerns the compounds of formula I wherein the substituents have various significances.

They are prepared by several processes including epimerizing replacement, treatment with cyanogen bromide or thiophosgene, treatment with an acid having a non-nucleophilic anion, treatment with dimethylsulfoxide and acetic anhydride, acylation, treatment with an oxalyl derivative and ammonia, methylation, oxidation, deprotection and protection.

They possess interesting pharmacological activity as antiinflammatory, immunosuppressant, antiproliferative and chemotherapeutic drug resistance reversing agents.

13 Claims, No Drawings

HETEROATOMS-CONTAINING TRICYCLIC COMPOUNDS

This application is a continuation in part of U.S. Pat. application Ser. No. 07/609,280 filed Nov. 5, 1990, now abandoned.

The invention relates to the field of macrolides. It concerns the compounds of formula I

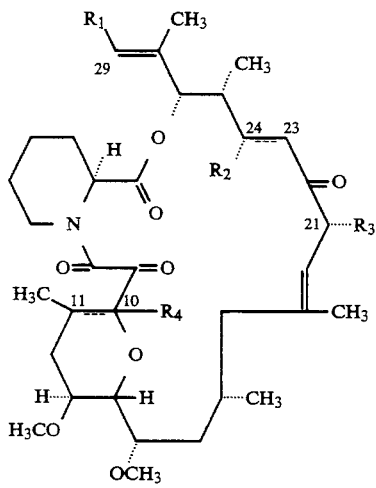

wherein
either $R_1$ is a group (a) of formula

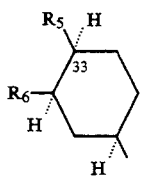

wherein
$R_5$ is chloro, bromo, iodo or azido and
$R_6$ is hydroxy or methoxy;
$R_2$ is oxo and there is a single bond in 23, 24 position; optionally protected hydroxy and there is a single or a double bond in 23,24 position; or absent and there is a double bond in 23,24 position; and
$R_4$ is hydroxy and there is a single bond in 10,11 position; or absent and there is a double bond in 10,11 position;
$R_1$ is a group (b) or (d) of formula

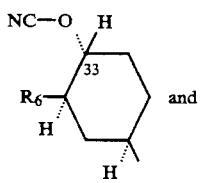

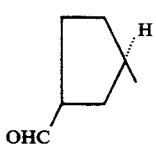

wherein $R_6$ is as defined above;

$R_2$ is as defined above; and
$R_4$ is hydroxy and there is a single bond in 10,11 position;
$R_1$ is a group (c) of formula

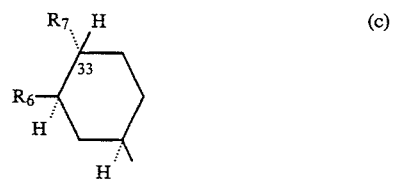

wherein
$R_6$ is as defined above and
$R_7$ is oxo; optionally protected hydroxy; methoxy; methylthiomethoxy; isobutanoyloxy; aminooxalyloxy; $R_8R_9CHCOO$— wherein $R_8$ is optionally protected hydroxy or optionally protected amino and $R_9$ is hydrogen or methyl; or p-tolyloxythiocarbonyloxy;
$R_2$ is oxo and there is a single bond in 23,24 position; absent and there is a double bond in 23,24 position; or is optionally protected hydroxy, methoxy, methylthiomethoxy, isobutanoyloxy, aminooxalyloxy or $R_8R_9CHCOO$— wherein $R_8$ and $R_9$ are as defined above, and there is a single or a double bond in 23,24 position;
whereby for group (c)
1) when $R_7$ is oxo, unprotected hydroxy or methoxy then $R_2$ is other than absent and other than unprotected hydroxy or methoxy, and there is a single bond in 23,24 position;
2) when $R_6$ is methoxy and $R_7$ is methylthiomethoxy then $R_2$ is other than absent and other than unprotected hydroxy;
3) when $R_6$ is methoxy and $R_7$ is protected hydroxy then $R_2$ is other than optionally protected hydroxy; and
4) when $R_6$ is hydroxy
then $R_7$ is other than optionally protected hydroxy; and
$R_4$ is hydroxy and there is a single bond in 10,11 position; and $R_3$ is methyl, ethyl, n-propyl or allyl;
in free form and, where such forms exist, in salt form, hereinafter referred to as "the compounds of the invention".

As is evident from formula I and the definition of the substituents when there is a single bond in 10,11 position the carbon atom to which the methyl group in 11 position is attached has the $\beta$-configuration and there is a hydrogen atom with the =-configuration attached to the carbon atom in 11 position; when there is a double bond in 10,11 position this methyl group lies-in the plane of the paper and there is no hydrogen atom in 11 position. When $R_2$ is oxo no hydrogen atom is attached to the carbon atom in 24 position. When $R_7$ is oxo the hydrogen atom shown in group (c) attached to the same carbon atom as $R_7$ is absent.

$R_1$ preferably is a group (c) or (d). $R_2$ preferably is unprotected hydroxy and there is a single bond in 23,24 position. $R_3$ preferably is ethyl or allyl. $R_4$ preferably is hydroxy. $R_5$ preferably is chloro. $R_6$ preferably is methoxy. $R_7$ preferably is isobutanoyloxy, aminooxalyloxy or $R_8R_9CHCOO$—. $R_8$ preferably is unprotected hydroxy or unprotected amino, especially unprotected hydroxy. $R_9$ preferably is hydrogen. When $R_9$ is other than hydrogen the carbon atom to which it is attached preferably has the (S) configuration.

Protected hydroxy preferably is hydroxy protected by a conventional hydroxy-protecting group such as formyl, tert-butoxycarbonyl, or trialkylsilyl; it especially is tert-butyldimethylsilyloxy.

Optionally protected hydroxy as defined above under formula I for $R_2$ and $R_7$ should not be understood as including a group $R_2$ or $R_7$ which is otherwise specified, such as e.g. aminooxalyloxy or $R_8R_9CHCOO-$.

Protected amino preferably is amino protected by a conventional amino-protecting group such as benzyloxycarbonyl or trialkylsilyl; it especially is tert-butoxycarbonyl.

A compound of the invention preferably is in free form. It preferably is in unprotected form.

A subgroup of compounds of the invention is the compounds $Ip_1$, i.e. the compounds of formula I wherein $R_1$ is a group (a) wherein $R_6$ is methoxy and
 either $R_5$ is chloro or bromo and
 $R_4$ is hydroxy and there is a single bond in 10,11 position
 or $R_5$ is azido and
 $R_4$ is hydroxy and there is a single bond in 10,11 position or absent and there is a double bond in 10,11 position;
$R_2$ is optionally protected hydroxy and there is a single or a double bond in 23,24 position; and
$R_3$ is as defined above under formula I;
in free form and, where such forms exist, in salt form.

A further subgroup of compounds of the invention is the compounds $Ip_2$, i.e. the compounds of formula I wherein $R_1$ is a group (c) wherein $R_6$ is methoxy and $R_7$ is oxo; optionally protected hydroxy; methoxy; methylthiomethoxy; aminooxalyloxy; $R_8CH_2COO-$ wherein $R_8$ is optionally protected amino; or p-tolyloxythiocarbonyloxy;
$R_2$ is absent and there is a double bond in 23,24 position; or optionally protected hydroxy, methoxy, methylthiomethoxy or aminooxalyloxy and there is a single or double bond in 23,24 position; whereby
 1) when $R_7$ is oxo, unprotected hydroxy or methoxy then $R_2$ is other than absent and other than unprotected hydroxy or methoxy, and
  there is a single bond in 23,24 position;
 2) when $R_7$ is methylthiomethoxy
  then $R_2$ is other than absent and other than unprotected hydroxy; and
 3) when $R_7$ is protected hydroxy
  then $R_2$ is other than optionally protected hydroxy; and
$R_4$ is hydroxy and there is a single bond in 10,11 position; and
$R_3$ is as defined above under formula I;
in free form and, where such forms exist, in salt form.

A further subgroup of compounds of the invention is the compounds $Ip_3$, i.e. the compounds of formula I wherein $R_1$ is a group (b) wherein $R_6$ is methoxy,
$R_2$ is optionally protected hydroxy and there is a single bond in 23,24 position; or absent and there is a double bond in 23,24 position;
$R_4$ is hydroxy and there is a single bond in 10,11 position; and
$R_3$ is as defined above under formula I;
in free form and, where such forms exist, in salt form.

A further subgroup of compounds of the invention is the compounds $Ip_4$, i.e. the compounds of formula I wherein $R_1$ is a group (d),
$R_2$ is optionally protected hydroxy and there is a single bond in 23,24 position; or absent and there is a double bond in 23,24 position;
$R_4$ is hydroxy and there is a single bond in 10,11 position; and
$R_3$ is as defined above under formula I;
in free form and, where such forms exist, in salt form.

A preferred subgroup of compounds of the invention is the compounds of formula I wherein $R_1$ is a group (a) wherein $R_5$ is as defined above under formula I and $R_6$ is methoxy;
$R_2$ is optionally protected hydroxy and there is a single bond in 23,24 position;
$R_4$ is hydroxy and there is a single bond in 23,24 position; or absent and there is a double bond in 10,11 position; and
$R_3$ is ethyl or allyl.

A further preferred group of compounds of the invention is the compounds of formula I wherein $R_1$ is a group (b) wherein $R_6$ is methoxy;
$R_2$ is optionally protected hydroxy and there is a single bond in 23,24 position; or absent and there is a double bond in 23,24 position;
$R_4$ is hydroxy and there is a single bond in 10,11 position; and
$R_3$ is ethyl or allyl.

A further preferred group of compounds of the invention is the compounds of formula I wherein $R_1$ is a group (c) wherein Re is methoxy and $R_7$ is as defined above under formula I;
$R_2$ is oxo and there is a single bond in 23,24 position; or optionally protected hydroxy, methylthiomethoxy, aminooxalyloxy, $R_8CH_2COO-$ wherein $R_8$ is optionally protected amino, and there is a single or a double bond in 23,24 position; whereby
 1) when $R_7$ is oxo, unprotected hydroxy or methoxy then $R_2$ is other than unprotected hydroxy or methoxy, and
  there is a single bond in 23,24 position;
 2) when $R_7$ is methylthiomethoxy
  then $R_2$ is other than unprotected hydroxy; and
 3) when $R_7$ is protected hydroxy
  then $R_2$ is other than optionally protected hydroxy;
$R_4$ is hydroxy and there is a single bond in 10,11 position; and
$R_3$ is ethyl or allyl.

A further preferred subgroup of compounds of the invention is the compounds of formula I wherein $R_1$ is a group (d),
$R_2$ is optionally protected hydroxy and there is a single bond in 23,24 position; or absent and there is a double bond in 23,24 position;
$R_4$ is hydroxy and there is a single bond in 10,11 position; and
$R_3$ is ethyl or allyl.

A further subgroup of compounds of the invention is the compounds Iq, i.e. the compounds of formula I wherein either $R_1$ is a group (a) wherein $R_5$ is chloro, bromo, iodo or azido and $R_6$ is hydroxy or methoxy,
$R_2$ is oxo and there is a single bond in 23,24 position; optionally protected hydroxy and there is a single or a double bond in 23,24 position; or absent and there is a double bond in 23,24 position; and $R_4$ is hydroxy and there is a single bond in 10,11 position; or absent and there is a double bond in 10,11 position;

or $R_1$ is a group (b) or (d) wherein $R_6$ is hydroxy or methoxy;

$R_2$ is as defined above for this subgroup; and $R_4$ is hydroxy and there is a single bond in 10,11 position;

or $R_1$ is a group (c) wherein $R_6$ is hydroxy or methoxy and $R_7$ is aminooxalyloxy; $R_8R_9CHCOO$— wherein $R_8$ is optionally protected hydroxy or optionally protected amino and $R_9$ is hydrogen or methyl; or p-tolyloxythiocarbonyloxy;

$R_2$ is methylthiomethoxy, isobutanoyloxy, amninooxalyloxy or $R_8R_9CHCOO$— wherein $R_8$ and $R_9$ are as defined above for this subgroup, and there is a single or double bond in 23,24 position; and $R_4$ is hydroxy and there is a single bond in 10,11 position; and $R_3$ is methyl, ethyl, n-propyl or allyl, in free form and, where such forms exist, in salt form.

A further subgroup of compounds of the invention is the compounds Ir, i.e. the compounds of formula I wherein either $R_1$ is a group (a) as defined above under formula I; and $R_2$ and $R_4$ have the significance indicated above under group (a);

or $R_1$ is a group (b) or (d) as defined above under formula I; and $R_2$ and $R_4$ have the significance indicated above under groups (b) and (d);

or $R_1$ is a group (c) as defined above under formula I wherein $R_6$ is as defined above under formula I and $R_7$ with the exception of optionally protected hydroxy has the significance indicated above under group (c);

whereby for group (c)

1) when $R_7$ is oxo or methoxy
then $R_2$ is other than absent and other than methoxy, and there is a single bond in 23,24 position; and 2) when $R_6$ is methoxy and $R_7$ is methylthiomethoxy
then $R_2$ is other than absent; and $R_4$ has the significance indicated above under group (c); and $R_3$ is as defined above under formula I;

in free form and, where such forms exist, in salt form.

In a subgroup of compounds Ir $R_7$ is other than oxo or methoxy; in a further subgroup when $R_6$ is methoxy then $R_7$ is other than methylthiomethoxy; in a further subgroup $R_2$ is other than absent and other than methoxy.

A further subgroup of compounds of the invention is the compounds of formula Is

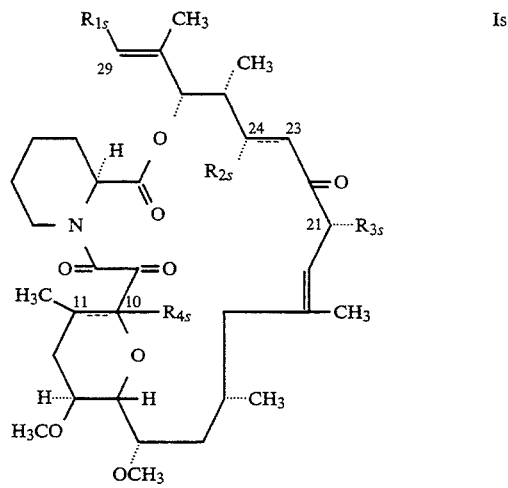

wherein either $R_{1s}$ is a group (a) wherein $R_5$ is chloro, bromo, iodo or azido and $R_6$ is methoxy;

$R_{2s}$ is hydroxy optionally protected by tert-butyldimethylsilyloxy and there is a single bond in 23,24 position; and $R_{4s}$ is hydroxy and there is a single bond in 10,11 position; or absent and there is a double bond in 10,11 position;

or $R_{1s}$ is a group (b) wherein Re is methoxy, or a group (d);

$R_{2s}$ is hydroxy optionally protected by tert-butyldimethylsilyloxy and there is a single bond in 23,24 position; or absent and there is a double bond in 23,24 position; and $R_{4s}$ is hydroxy and there is a single bond in 10,11 position;

or $R_{1s}$ is a group (c) wherein $R_6$ is methoxy and $R_7$ is oxo; hydroxy optionally protected by tert-butyldimethylsilyloxy; methoxy; methylthiomethoxy; isobutanoyloxy; aminooxalyloxy; $R_8R_9CHCOO$— wherein $R_8$ is hydroxy optionally protected by tert-butyldimethylsilyloxy or amino optionally protected by tert-butoxycarbonyl and $R_9$ is hydrogen or methyl; or p-tolyloxythiocarbonyloxy;

$R_{2s}$ is oxo and there is a single bond in 23,24 position; absent and there is a double bond in 23,24 position; or is hydroxy optionally protected by tert-butyldimethylsilyloxy, methoxy, methylthiomethoxy, aminooxalyloxy or $R_8R_9CHCOO$— wherein $R_8$ is amino optionally protected by tert-butoxycarbonyl and $R_9$ is hydrogen, and there is a single bond in 23,24 position;

whereby for group (c)

1) when $R_7$ is oxo, unprotected hydroxy or methoxy
then $R_{2s}$ is other than absent and other than unprotected hydroxy or methoxy, and
there is a single bond in 23,24 position;

2) when $R_7$ is methylthiomethoxy
then $R_{2s}$ is other than absent and other than unprotected hydroxy; and 3) when $R_7$ is hydroxy protected by tert-butyldimethylsilyloxy
then $R_{2s}$ is other than hydroxy optionally protected by tert-butyldimethylsilyloxy; and $R_{4s}$ is hydroxy and there is a single bond in 10,11 position; and $R_{3s}$ is ethyl or allyl, in free form and, where such forms exist, in salt form.

A compound of the invention can be obtained by a process comprising a) for the preparation of a compound of formula I wherein $R_1$ is a group (a) as defined above under formula I, $R_2$ and $R_3$ are as defined above under formula I and $R_4$ is hydroxy (i.e. a compound Ia), replacing under simultaneous epimerization the hydroxy group by chlorine, bromine, iodine or azido in a corresponding compound having unprotected hydroxy in 33 position (i.e. a compound IIa, of formula IIa

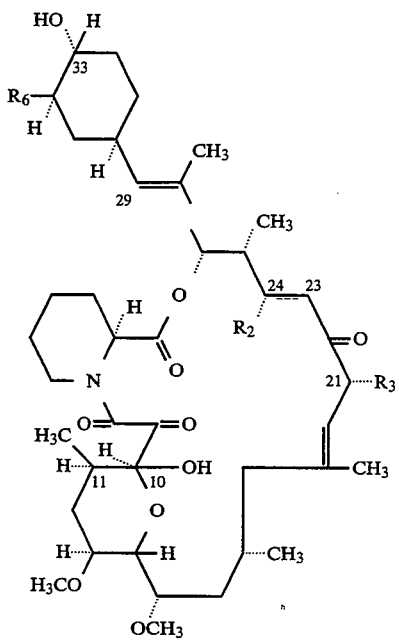

IIa wherein $R_2$ and $R_3$ are as defined above under formula I and $R_6$ is hydroxy or methoxy);

b) for the preparation of a compound of formula I wherein $R_1$ is a group (b) as defined above under formula I, $R_2$ and $R_3$ are as defined above under formula I and $R_4$ is hydroxy (i.e. a compound Ib), treating a corresponding compound IIa with cyanogen bromide in the presence of a base or treating a corresponding compound IIa with thiophosgene, reacting the resultant product with an inorganic azide and allowing the resultant unstable intermediate having a group

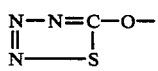

in 33 position (i.e. a compound IIb) to decompose to a corresponding compound Ib;

c) for the preparation of a compound of formula I wherein $R_1$ is a group (d) as defined above under formula I, $R_2$ and $R_3$ are as defined above under formula I and $R_4$ is hydroxy (i.e. a compound Ic), treating a corresponding compound Ib with an acid having a non-nucleophilic anion;

d) for the preparation of a compound of formula I wherein $R_1$ is a group (c) wherein Re is as defined above under formula I, one of $R_2$ and $R_7$ is oxo or methylthiomethoxy and the other is protected hydroxy, $R_3$ is as defined above under formula I and $R_4$ is hydroxy (i.e. a compound Id), treating a corresponding compound wherein one of the substituents in 24 and 33 position is hydroxy and the other is protected hydroxy, (i.e. a compound IIc) with dimethylsulfoxide and acetanhydride;

e) for the preparation of a compound of formula I wherein $R_1$ is a group (c) wherein $R_6$ is as defined above under formula I and $R_7$ is isobutanoyloxy, aminooxalyloxy, $R_8R_9CHCOO-$ as defined above under formula I or p-tolyloxythiocarbonyloxy, $R_2$ and $R_3$ are as defined above under formula I and $R_4$ is hydroxy (i.e. a compound Ie), appropriately acylating a corresponding compound IIa;

f) for the preparation of a compound of formula I wherein $R_1$ is a group (c) wherein $R_6$ is as defined above under formula I and $R_7$ is aminooxalyloxy, $R_2$ is optionally protected hydroxy or is aminooxalyloxy, $R_3$ is as defined above under formula I and $R_4$ is hydroxy (i.e. a compound If), treating with an appropriate oxalyl derivative and thereafter with ammonia a corresponding compound having an optionally protected hydroxy group in 33 position and a protected hydroxy group in 24 position (i.e. a compound IId);

g) for the preparation of a compound of formula I wherein $R_1$ is a group (c) wherein $R_6$ is as defined above under formula I, $R_2$ and $R_7$ are as defined above under formula I with the proviso that one of $R_2$ and $R_7$ is methoxy, $R_3$ is as defined above under formula I and $R_4$ is hydroxy (i.e. a compound Ig), methylating a corresponding compound having a hydroxy group in 24 or 33 position (i.e. a compound IIe);

h) for the preparation of a compound of formula I wherein $R_1$ is a group (c) wherein $R_6$ is as defined above under formula I, $R_2$ and $R_7$ are as defined above under formula I with the proviso that one of $R_2$ and $R_7$ is oxo, $R_3$ is as defined above under formula I and $R_4$ is hydroxy (i.e. a compound Ih), oxidizing a corresponding compound having a hydroxy group in 24 or 33 position (i.e. a compound IIf); and when a resultant compound of formula I has a protected hydroxy and/or a protected amino group, optionally splitting off the protecting group(s) to give a corresponding compound of formula I having one or more unprotected hydroxy and/or unprotected amino group(s) (i.e. a compound Ij), whereby when $R_1$ is a group (a), a water molecule may be simultaneously split off and a compound of formula I is obtained wherein $R_1$ is a group (a) as defined above under formula I, $R_2$ is unprotected hydroxy and there is a single or double bond in 23,24 position; and $R_4$ is absent and there is a double bond in 10,11 position (i.e. a compound Ii); or optionally protecting an unprotected hydroxy and/or unprotected amino group in a resultant compound of formula I as appropriate to give a corresponding compound of formula I having one or more protected hydroxy and/or protected amino groups(s) (i.e. a compound Ik), and recovering the resultant compound of formula I in free form and, where such forms exist, in salt form.

The process variants of the invention can be effected in a manner analogous to known procedures.

Process variant a) is a substitution reaction under simultaneous epimerization. It is preferably effected in an inert solvent such as tetrahydrofurane or toluene. Preferably for the substitution by halogen the reaction is effected with tetrachloro-, tetrabromo- or tetraiodomethane in the presence of triphenylphosphine, and for the substitution by azido with azodicarboxylic acid ester, preferably diethyl ester, and hydrazoic acid. A hydroxy group in 24 position may be in protected form. As protecting group known hydroxy protecting groups such as tert-butyldimethylsilyl may be used. A protecting group may subsequently be split off in accordance with known procedures, e.g. with hydrofluoric acid in acetonitrile. Upon deprotection a water molecule may, depending on the reaction conditions chosen, simultaneously be split off in position 10,11 and a double bond formed. The individual compounds can be separated from such a resultant mixture in conventional manner, e.g. chromatographically.

Compounds Ia may be further processed by e.g. oxidation or dehydration to corresponding compounds wherein $R_4$ is absent; for example, oxidation of compounds Ia wherein $R_2$ is hydroxy leads to corresponding compounds wherein $R_4$ is absent and $R_2$ is oxo.

Process variant b) is a cyanidation reaction. It preferably is effected in an inert solvent such as a chlorinated hydrocarbon, e.g. dichloromethane. The temperature preferably is about room temperature. The base is e.g. 4-dimethylaminopyridine.

A compound of formula I obtained accordance to process variants a) and b) above may be isolated from the reaction mixture and purified in accordance with known methods. When $R_2$ is hydroxy and there is a single bond in 23,24 position a water molecule may be simultaneously split off. A corresponding mixture of compounds Ib is obtained wherein either $R_2$ is hydroxy and there is a single bond in 23,24 position or $R_2$ is absent and there is a double bond in 23,24 position. The individual compounds can be separated from such a resultant mixture in conventional manner, e.g. chromatographically.

The second procedure according to process variant b) is effected by reaction with thiophosgene, preferably in the presence of an acid scavenger such as 4-dimethylaminopyridine. Preferably an inert solvent such as acetonitrile is used. The temperature preferably is about room temperature. The subsequent reaction with an inorganic azide is preferably effected with sodium azide. The resultant compounds IIb are unstable and decompose already at room temperature to compounds Ib, under splitting off of nitrogen and sulfur. This reaction step preferably is effected in an inert solvent such as an aromatic hydrocarbon, e.g. benzene. Temperature preferably is elevated, e.g. about 50° C.

In process variant c) a ring contraction takes place. Protecting groups which are present may be simultaneously split off. Preferably an inert solvent such as acetonitrile is used. Preferably hydrofluoric acid is used as acid having a non-nucleophilic anion. Temperature preferably is about room temperature.

Process variant d) is a Swern oxidation. The reaction preferably is effected with compound IIc dissolved in dimethylsulfoxide and acetic arthydride. Duration of reaction is prolonged, e.g. about 5 hours. Temperature preferably is about room temperature.

Process variant e) is an acylation. It is preferably effected in an inert solvent such as acetonitrile. The acylating agent preferably is an activated acyl derivative, such as an acyl halogenide or anhydride. An acid scavenger such as dimethylaminopyridine or pyridine is employed. Further, a compound IIa may also be reacted with a carboxylic acid such as glycine protected at the amino moiety by e.g. tert-butoxycarbonyl, or with a compound of formula $R_8R_9CHCOOH$ wherein $R_8$ is protected hydroxy and $R_9$ is hydrogen or methyl, and a carbodiimide such as N-ethyl-N'-(3-dimethylaminopropyl)carbodiimide or N,N'-dicyclo-hexylcarbodiimide where indicated in the presence of a base, such as 4-dimethylaminopyridine, preferably in an inert solvent such as acetonitrile or in a chlorinated hydrocarbon. An amino protecting group may subsequently be split off together with any hydroxy protecting group which may be present. If in the starting compound IIa $R_2$ is hydroxy and there is a single bond in 23,24 position, upon acylation splitting off of a water molecule in 23,24 position may occur and a compound Ie be formed wherein $R_2$ is absent and there is a double bond in 23,24 position.

Process variant f) is an acylation. It is preferably effected in an inert solvent such as acetonitrile. Temperature preferably is reduced, e.g. about 0° to 5° C. The oxalyl derivative preferably is an oxalyl halogenide, e.g. chloride. Upon completion of the reaction the mixture is stirred with ammonia.

Process variant g) is a methylation. It preferably is effected in an inert solvent such as a chlorinated hydrocarbon, e.g. dichloromethane. The methylating agent preferably is diazomethane in the presence of e.g. borotrifluoride-etherate. Temperature preferably is from about 0° to about room temperature.

Process variant h) is an oxidation. The oxidizing agent is e.g. tetrapropylammonium perruthenate. The temperature preferably is about room temperature.

The optional deprotection process variant may also be effect in conventional manner. For splitting off of e.g. tert-butyldimethylsilyl it is effected by treatment with e.g. hydrofluoric acid in a solvent such as acetonitrile. Depending on the reaction conditions selected (duration, temperature, etc.) the splitting can be steered in such a manner that either all or only some protecting group are removed. Partial deprotection is particularly indicated where a definite hydroxy group is to be subsequently reacted in a later reaction.

The optional protection step variant may also be effected in conventional manner along similar lines.

Thus for subsequent reactions involving a hydroxy group, particularly a hydroxy group in position 24 and/or 33, selective protection of only one of the two free hydroxy groups or selective deprotection of only one of the two protected hydroxy groups may be effected in such a manner that reaction occurs only at the desired position. Mixtures of end products may be obtained thereby; such mixtures can be separated in conventional manner, e.g chromatographically. Resultant end products still containing protecting groups can be subsequently deprotected. Reaction conditions may alternatively be selected such that simultaneously with or immediately after reaction the protecting groups-are removed (one pot process).

The compounds of formula I may be isolated and purified from the reaction mixture in conventional manner.

Insofar as their preparation is not specifically described herein, e.g. in the Examples, the compounds used as starting materials are known or can be obtained in conventional manner from known compounds, e.g. starting from appropriate Streptomyces strains such as Streptomyces tsukubaensis No. 9993 described in e.g. Fujisawa EP 184162. Samples can be obtained from the Fermentation Research Institute, Tsukuba, Ibaraki 305, Japan under provisions of the Budapest Treaty under deposit No. FERM BP-927. This strain has been redeposited on Apr. 27, 1989 e.g. as disclosed in Sandoz EP 356399, with the Agricultural Research Culture Collection international Depository, Peoria, Illinois 61604, USA under the provisions of the Budapest Treaty under deposit No. NRRL 18488.

The following Examples illustrate the invention and are not limitative. All temperatures are in degrees Centigrade. All NMR spectra are in CDCl$_3$, ppm. The abbreviations have the following meanings:

BOC: tert-butoxycarbonyl;
cfr: colourless foamy resin:
db: double bond;
Et: ethyl;
FK 506: the compound of formula

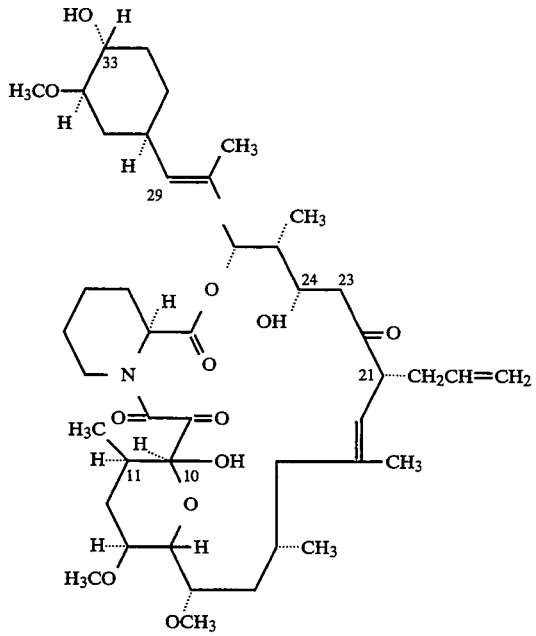

i.e. b 17α-allyl-1β, 14α-dihydroxy-12-[2'-(4"(R)-hydroxy3"(R)-methoxycyclohex -1"(R)-1'-methyl-trans-vinyl]-23α,25β-dimethoxy-13α,19,21α,27β-tetramethyl-11,28-dioxa -4-azatricyclo[22.3.1.0$^{4,}$-9]octacos-18-trans-ene-2,3,10,16-tetraone (according to the atom numbering in EP 184162; however, in the Examples the atom numbering of formula I is used throughout);

FR 520: as FK 506, but with ... CH$_2$CH$_3$ (ethyl) in place of allyl in position 21 in the formula;

iBuoyloxy: isobutanoyloxy [(H$_3$C)$_2$CHCOO—];
iPr: isopropyl;
na: not applicable;
N$_3$: azido;
OMe (or MeO): methoxy;
OtBDMS: tert-butyldimethylsilyloxy;
sb: single bond;
tBu: tert-butyl.

EXAMPLE 1

24-tert-Butyldimethylsilyloxy-33-epi-33-chloro-FK506

[Formula I: R$_1$ = a group (a) wherein R$_5$ = chloro, R$_6$ = OMe; R$_2$ = OtBDMS, single bond in 23,24 position; R$_3$ = allyl; R$_4$ = OH, single bond in 10,11 position]

[Process variant a), replacement with epimerization]

0.092 g 24-tert-butyldimethylsilyloxy-FK506 is heated for 15 hours under refluxing with 0.037 g triphenylphosphine in 4 ml of tetrachloromethane. The solvent is evaporated to dryness under reduced pressure and the residue is purified by column chromatography over silicagel using a mixture of hexane and acetic acid ethyl ester (2:1) as the eluant. The title compound is obtained (colourless foam):

$^1$H-NMR: about 2:3 mixture of conformers: main conformer: 4.56 (m, w$_½$= 7 Hz, H-33).

The starting material is obtained as follows:

a) 20 g FK 506 is dissolved in 400 ml of dry dimethylformamide, 5.08 g imidazole and 11.25 g tert-butyldimethylchlorosilane is added in portions and the mixture is stirred for 110 hours at room temperature. The reaction mixture is diluted with acetic acid ethyl ester and washed five times with water. The organic phase is dried over sodium sulfate and the solvent distilled off under reduced pressure. The resultant crude product is purified by chromatography over silicagel using hexane/acetic acid ethyl ester 3:1 as the eluant. 24,33-Bis-(tert-butyldimethylsilyloxy)-FK 506 is obtained:

$^{13}$C-NMR: main conformer: 69.7 (C-24); 75.1 (C-33); 84.1 (C-32); 164.6 (C-8); 168.9 (C-1); 196.4 (C-9); 209.3 (C-22); minor conformer: 70.9 (C-24); 75.3 (C-33); 84.1 (C-32); 165.8 (C-8); 168.2 (C-1); 191.2 (C-9); 210.0 (C-22);

b) 0.5 g 24,33-bis-(tert-butyldimethylsilyloxy)-FK506 is dissolved at 0° under stirring into a mixture of 10 ml of acetonitrile and 0.5 ml of 40% hydrofluoric acid. After 2 hours at that temperature the reaction medium is diluted with dichloromethane. The solution is washed successively with saturated aqueous sodium bicarbonate solution and water, and the organic phase dried over sodium sulfate, and the solvent is evaporation under reduced pressure. the resultant residue is purified by column chromatography over silicagel (eluant: dichloromethane/methanol 9:1). 24-tert-Butyldimethylsilyloxy-FK506 is obtained as a colourless foam:

$^{13}$C-NMR: main conformer: 69.7 (C-24); 73.6 (C-33); 84.1 (C-32); 164.6 (C-8); 168.9 (C-1); 196.4 (C-9); 209.2 (C-22); minor conformer: 70.7 (C-24); 73.6 (C-33); 84.2 (C-32); 165.8 (C-8); 168.2 (C-1); 191.4 (C-9); 209.2 (C-22).

EXAMPLE 2

24-tert-Butyldimethylsilyloxy-33-epi-33-azido-FK506

[Formula I: R$_1$ = a group (a) wherein R$_5$ = azido, R$_6$ = OMe; R$_2$ = OtBDMS, single bond in 23,24 position; R$_3$ = allyl; R$_4$ = OH, single bond in 10,11 position]

[Process variant a)]

To a solution of 0.092 g 24-tert-butyldimethyl-silyloxy-FK506 and 0.08 g triphenylphosphine in 2 ml of dry tetrahydrofurane is added at 0° 0.047 ml of azodicarboxylic acid diethyl ester, followed by 0.15 ml of a 2 M solution of hydrazoic acid in toluene. The solution is brought to room temperature and stirred for 18 hours. The solvent is evaporated to dryness under reduced pressure and the residue purified as described above under Example 1. The title compound is obtained (colourless foam):

$^1$H-NMR: 4.07 (m, H-33).

EXAMPLE 8

24-tert-Butyldimethylsilyloxy-33-cyanoxy-FR 520

[Formula I: as for Example 7]
[Process variant b), treatment with thiophosgene and sodium azide]

A solution of 2 g 24-tert-butyldimethylsilyloxy-FR 520 and 2 g 4-dimethylaminopyridine in 50 ml of acetonitrile is carefully reacted with 0.4 ml of thiophosgene and the mixture stirred for 3 hours at room temperature. The reaction mixture is poured onto a well-stirred mixture consisting of 150 ml of acetic acid ethyl ester, 40 ml

| Example No. | Analogous to Ex. No. | $R_1$ | $R_5$ | $R_6$ | $R_7$ | $R_2$ | Position 23,24 | $R_3$ | $R_4$ | Position 10,11 | Physicochemical characterization data |
|---|---|---|---|---|---|---|---|---|---|---|---|
| 3 | 1[1)] | (a) | Cl | OMe | na | OtBDMS | sb | Et | OH | sb | NMR* |
| 4 | 1[1)] | (a) | Br | OMe | na | OtBDMS | sb | Et | OH | sb | |
| 5 | 1 | (a) | Br | OMe | na | OtBDMS | sb | allyl | OH | sb | |
| 6 | 2[1)] | (a) | $N_3$ | OMe | na | OtBDMS | sb | Et | OH | sb | |
| 6a | 1[1)] | (a) | I | OMe | na | OtBDMS | sb | Et | OH | sb | NMR* |

*NMR:

Example 3: $^1$H-NMR: 4.56(m, H-33);

Example 6a: $^{13}$C-NMR: mixture of conformers: 210.33(C-22); 168.91(C-1); 164.59(C-8); 123.64(C-20); 78.90(C-32); 25.81(tBu);

[1)]The starting material is obtained from FR 520 in a manner analogous to 24-tert-butyldimethylsilyloxy-FK 506 (see Example 1):

a) 24,33-bis-(tert-butyldimethylsilyloxy)-FR 520: $^1$H-NMR: about 2:1 mixture of 2 conformers:

main conformer: 4.42(m, H-2); 4.41(db, 13Hz, H-6eq.); 4.05(txt, J=1.5Hz and 6Hz, H-24); 3.80(dxd, J=1.5Hz and 10Hz, H-14); 2.95(dxdxd, J=4Hz, 8Hz and 11Hz, H-32);

minor conformer: 4.25(q, J=5Hz, H-24); 3.94(dxd, J=2Hz and 10Hz, H-14); 2.95(dxdxd, J=4Hz, 8Hz and 11Hz, H-32);

b) 24-tert-butyldimethylsilyloxy-FR 520: $^1$H-NMR: about 2:1 mixture of 2 conformers:

main conformer: 4.44(b, H-2); 4.42(db, J=13Hz, H-6eq.); 4.05(dxt, J=1,5Hz and 6Hz, H-24); 3.81(dxd, J=1.5Hz and 10Hz, H-14); 3.01(dxdxd, J=4Hz, 8Hz and 11Hz, H-32);

minor conformer: 4.24(H-24); 3.94(dxd, J=2Hz and 10Hz, H-14); 3.01(dxdxd, J=4Hz, 8Hz and 11Hz, H-32).

EXAMPLE 7

24-tert-Butyldimethylsilyloxy-33-cyanoxy-FR 520

[Formula I: $R_1$ = a group (b) wherein $R_6$ = OMe; $R_2$ = OtBDMS, single bond in 23,24 position; $R_3$ = Et; $R_4$ = OH, single bond in 10,11 position]

[Process variant b), treatment with cyanogen bromide]

A solution of 2 g 24-tert-butyldimethylsilyloxy-FR 520 and 0.94 g 4-dimethylaminopyridine in 100 ml of dichloromethane is rapidly reacted at room temperature with a solution of 0.4 g cyanogen bromide in 15 ml of dichloromethane and the mixture is stirred at room temperature for 20 minutes. The mixture is filtered over silicagel (eluant: n-hexane/acetic acid ethyl ester) and the solvent is removed from the relevant fraction under reduced pressure. The title compound is obtained as a colourless foamy resin:

$^1$H-NMR: mixture of conformers: 4.3 (m; H-33).

of saturated aqueous sodium chloride solution and 50 ml of 2 N sodium azide solution, vigourous stirring is continued for 5 minutes and the organic phase is separated. The organic phase is then successively washed with water, 1N hydrochloric acid solution, water, and saturated aqueous sodium chloride solution, dried over sodium sulfate, filtered and concentrated under reduced pressure. The residue is taken up in about 100 ml of benzene and heated at 30°–40° for 2 hours. The benzene is removed under reduced pressure and the title compound is recovered from the residue as a colourless foamy resin by column chromatography over silicagel (eluant: n-hexane / acetic acid ethyl ester):

$^1$H-NMR: see Example 7.

| Example No. | Analogous to Ex. No. | $R_1$ | $R_5$ | $R_6$ | $R_7$ | $R_2$ | Position 23,24 | $R_3$ | $R_4$ | Position 10,11 | Physicochemical characterization data |
|---|---|---|---|---|---|---|---|---|---|---|---|
| 9 | 7,8 | (b) | na | OMe | na | OtBDMS | sb | allyl | OH | sb | NMR* |
| 10a[1)] | 7,8 | (b) | na | OMe | na | OH | sb | Et | OH | sb | NMR* |
| 10b[1)] | 7,8 | (b) | na | OMe | na | absent | db | Et | OH | sb | NMR* |
| 11a[2)] | 7,8 | (b) | na | OMe | na | OH | sb | allyl | OH | sb | |
| 11b[2)] | 7,8 | (b) | na | OMe | na | absent | db | allyl | OH | sb | |

*NMR:

Example 9: $^1$H-NMR: mixture of conformers: 4.3(m, H-33);

Example 10a: $^1$H-NMR: mixture of conformers: 5.34(H-26); 4.63(db, J=4Hz, H-2); 4.44(db, J=13Hz, H-6eq.); 4.30(dxdxd, J=5Hz, 8Hz and 11Hz, H-33); 3.01(tb, J=13Hz, H-6ax.);

Example 10b: $^1$H-NMR: 6.81 resp. 6.75(dxd resp. dxd, J=5Hz and 15Hz resp. 7Hz and 15Hz, H-24); 6.2 resp. 6.3(dxd resp. dxd, J=2Hz and 15Hz resp. 1Hz and 15Hz, H-23); 5.29 resp. 5.23(d resp. d, J=3Hz resp. 3Hz, H-26); 4.3(m, H-33);

[1),2)]A mixture of both compounds is obtained; they can be separated chromatographically (eluant: n-hexane/acetic acid ethyl ester).

EXAMPLE 12

29-Des-(4-hydroxy-3-methoxycyclohexyl)-29-(3-formylcyclopentyl)-FR 520

[Formula I: $R_1$ = a group (d); $R_2$ = OH, single bond in 23,24 position; $R_3$ = Et; $R_4$ = OH, single bond in 10,11 position]

[Process variant c), treatment with a non-nucleophilic anion]

0.5 g 24-tert-butyldimethylsilyloxy-33-cyanoxy-FK 520 (compound of Examples 7 and 8) or 33-cyanoxy-FR 520 (compound of Example 10a) is dissolved into a mixture of 50 ml of acetonitrile and 2 ml of 40% wt. aqueous hydrofluoric acid and the mixture is stirred for 2.5 hours at room temperature. The reaction mixture is then distributed between acetic acid ethyl ester and saturated aqueous sodium bicarbonate solution, the aqueous phase is discarded and the organic phase is washed with saturated aqueous sodium chloride solution, dried over sodium sulfate, filtered and concentrated under reduced pressure. The title compound obtained as a colourless foamy resin from the residue by column chromatography over silicagel (eluant: n-hexane / acetic acid ethyl ester):

$^1$H-NMR: mixture of conformers: 9.64 (d, J=2 Hz, CHO); 2.87 (m, H-32); 2.67 (m, H-30).

of the residue over silicagel (eluant: acetic acid ethyl ester / n-hexane 2:1) the title compounds are obtained as colourless foamy resins:

compound a): $^{13}$C-NMR: about 2:1 mixture of conformers: 209.3/209.9 (C-22); 208.3/208.5 (C-33); 196.4 (C-9); 168.9/168.2 (C-1); 164.6/165.9 (C-8); 138.5/139.4 (C-19); 135.6/136.1 (C-37); 133.4/134.1 (C-28); 131.8/127.6 (C-29); 123.1/122.3 (C-20); 116.5/116.1 (C-38); 97.6/98.9 (C-10); 83.0 (C-32); 69.6/70.6 (C-24);

compound b): $^1$H-NMR: about 2:1 mixture of conformers: 4.82/4.79 (A3; $J_{AB}$=12 Hz; —O—CH$_2$—S); 2.19 resp. 2.18 (s resp. s, —SCH$_3$);

| Example No. | Analogous to Ex. No. | R$_1$ | R$_5$ | R$_6$ | R$_7$ | R$_2$ | Position 23,24 | R$_3$ | R$_4$ | Position 10,11 | Physicochemical characterization data |
|---|---|---|---|---|---|---|---|---|---|---|---|
| 16a | 15[1)] | (c) | na | OMe | OtBDMS | OCH$_2$SCH$_3$ | sb | allyl | OH | sb | cfr; NMR* |
| 16b | 15[1)] | (c) | na | OMe | OtBDMS | oxo | sb | allyl | OH | sb | cfr; NMR* |
| 16c | 15[2)] | (c) | na | OMe | oxo | OtBDMS | sb | Et | OH | sb | cfr |
| 16d | 15[3)] | (c) | na | OMe | OtBDMS | oxo | sb | Et | OH | sb | cfr |

[1)]Starting from 33-tert-butyldimethylsilyloxy-FK 506 (compound of Example 16 in EP 184162); eluant: toluene/acetic acid ethyl ester 9:1;
[2)]Starting from 24-tert-butyldimethylsilyloxy-FR 520;
[3)]Starting from 33-tert-butyldimethylsilyloxy-FR 520 (DOS 39 38 754);
*NMR:
Example 16a: $^1$H-NMR: about 2:1 mixture of conformers: 4.36(s, —O—CH$_2$—S) and 2.16(s, —SCH$_3$) resp. 4.37 and 4.40(AB, —O—CH$_2$—S) and 2.13(s, —SCH$_3$);
Example 16b:
$^1$H-NMR: about 1:1 mixture of conformers: 5.29 and 5.59(s, H-23);
$^{13}$C-NMR: about 1:1 mixture of conformers: 200.7/197.7(C-22); 195.3/194.9(C-24); 193.2/189.6(C-9); 168.9/169.1(C-1); 164.4/165.2(C-8); 137.5/137.9(C-19); 135.1/135.3(C-37); 130.1/131.1(C-24); 130.1/129.3(C-28); 123.9/123.7(C-20); 116.7/116.7(C-38); 98.7/98.0(C-10); 96.3/97.8(C-23).

EXAMPLE 17

33-p-Tolyloxythiocarbonyloxy-FK 506

[Formula I: R$_1$ = a group (c) wherein R$_6$ = OMe, R$_7$ = p-tolyloxythiocarbonyloxy; R$_2$ = OH, single bond in 23, 24 position; R$_3$ = allyl; R$_4$ = OH, single bond in 10,11 position]

| Example No. | Analogous to Ex. No. | R$_1$ | R$_5$ | R$_6$ | R$_7$ | R$_2$ | Position 23,24 | R$_3$ | R$_4$ | Position 10,11 | Physicochemical characterization data |
|---|---|---|---|---|---|---|---|---|---|---|---|
| 13 | 12[1)] | (d) | na | na | na | OH | sb | allyl | OH | sb | NMR* |
| 14 | 12[2)] | (d) | na | na | na | absent | db | Et | OH | sb | NMR* |

*NMR:
Example 13: $^1$H-NMR: mixture of conformers: 9.65(d, J=2Hz, CHO); 2.86(m, H-32); 2.15(dxdxd, J=12.5Hz and 7.5Hz and 5Hz, H-31a); 1.45(dxt, J=12.5 and 9Hz, H-31b); 2.67(m, H-30);
Example 14: $^1$H-NMR: about 5:3 mixture of conformers: 9.66(d, J=2Hz, CHO); 6.83(dxd, J=15 and 5Hz) resp. 6.77(dxd, J=15 and 7.5Hz)H-24; 6.19(dxd, J=15 and 1.5Hz) resp. 6.30(dxd, J=15 and 1Hz)H-23;
[1)]Starting from the compound of Example 9 or 11a;
[2)]Starting from the compound of Example 10b.

EXAMPLE 15 a) 24-tert-Butyldimethylsilyloxy-33-oxo-FK 506 and
b) 24-tert-Butyldimethylsilyoxy-33-methylthiomethoxy FK 506

Formula I: R$_1$ = a group (c) wherein R$_6$ = OMe, R$_7$ = oxo and, respectively, methylthiomethoxy; R$_2$ = OtBDMS, single bond in 23,24 position; R$_3$ = allyl; R$_4$ = OH, single bond in 10,11 position]

Process variant d), treatment with dimethylsulfoxide and acetanhydride]

1 g 24-tert-Butyldimethylsilyloxy-FK 506 is dissolved at room temperature into a mixture o#20 ml of acetanhydride and 30 ml of dimethylsulfoxide and stirring is effected for 5 hours at room temperature. The reaction mixture is poured onto a mixture of acetic acid ethyl ester and potassium carbonate solution, stirred for 20 minutes, the phases are separated and the organic phase is repeatedly washed with water, dried over sodium sulfate filtered and concentrated under reduced pressure. Following column chromatographic fractionation

[Process variant e), acylation]

A solution of 2 g FK506 in 70 ml of acetonitrile is successively reacted with 0.46 g 4-dimethylaminopyridine and 1.8 g p-tolyloxythiocarbonyl chloride and the mixture is stirred for 15 hours at room temperature. The reaction mixture is then diluted with acetic acid ethyl ester and successively washed with saturated aqueous sodium bicarbonate solution, 0.5 N hydrochloric acid and water, dried over sodium sulfate, filtered and concentrated under reduced pressure. The title compound is isolated from the residue as a light yellow foamy resin by column chromatography over silicagel (eluant: acetic acid ethyl ester /n-hexane 1:1):

$^1$H-NMR: 7.22 and 7.01 (AABB-syst., at-H); 5.35 (d, J=1 Hz, H-26); 5.18 (dxdxd, J=5 Hz, 9.5 Hz and 11Hz, H-33); 3.475, 3.47, 3.41, 3.40, 3.355 and 3.32 (each s, —OCH$_3$); 2.38 (s, ar-CH$_3$);

EXAMPLE 18

33-Aminomethylcarbonyloxy-$\Delta^{23}$-FK 506

[Formula I: $R_1$ = a group (c) wherein $R_6$ = OMe, $R_7$ = $R_8R_9$CHCOO— ($R_8$ = amino; $R_9$ = H); $R_2$ = absent, double bond in 23,24 position; $R_3$ = allyl; $R_4$ = OH, single bond in 10,11 position]

[Process variant e)]

2 g N-BOC-glycine, 1 g dicyclohexylcarbodiimide, 0.5 g $\Delta^{23}$-FK 506 (second compound of Example 17 in EP 184162) and 1 g 4-dimethylaminopyridine are successively taken up at room temperature in 70 ml of acetonitrile and the mixture is stirred for 20 minutes at room temperature. The reaction mixture is filtered, the filtrate diluted with acetic acid ethyl ester and successively washed with 1 N hydrochloric acid, aqueous Sodium bicarbonate solution and water and the organic phase is dried over sodium sulfate, filtered, concentrated, and the residue is taken up in 50 ml of acetonitrile.

In order to split off the protecting group 0.5 g p-toluenesulfonic acid monohydrate is added and the mixture heated to refluxing for 5 minutes, the solution is cooled off, diluted with acetic acid ethyl ester, washed to neutrality with water, and the organic phase is dried over sodium sulfate and concentrated. From the residue the title compound is obtained as a colourless foamy resin after column chromatography over silicagel (eluant: acetic acid ethyl ester /methanol 20:3):

$^1$H-NMR: about 6:5 mixture of conformers: 6.81 (dxd, J-5 Hz and 15 Hz) resp. 6.76 (dxd, J=7.5 Hz and 15 Hz) H-24; 6.18 (dxd, J-1 Hz and 15 Hz) resp. 6.29 (dxd, J=1 Hz and 15 Hz) H-23; 4.77 (m, H-33);

EXAMPLE 19

24-tert-Butyldimethylsilyloxy-FR 520
33-[(tert-butyldimethylsilyloxy)-(S)-lactate]

[Formula I: $R_1$ = a group (c) wherein $R_6$ = OMe, $R_7$ = $R_8R_9$CHCOO—($R_8$ = OtBDMS, $R_9$ = Me, S-configuration); $R_2$ = OtBDMS, single bond in 23,24 position; $R_3$ = $R_4$ = OK, single bond in 10,11 position]

[Process variant e)]

To a solution of 450 mg 24-tert-butyldimethylsilyloxy-FR 520 and 120 mg tert-butyldimethylsilyloxy-(S)-lactic acid in 10 ml of dichloromethane are added at room temperature 120 mg N-ethyl-N'-(3-dimethylaminopropyl)carbodiimide hydrochloride and 23 mg dimethylaminopyridine. After 60 hours the reaction mixture is diluted with acetic acid ethyl ester, washed with successively. 0.5 N hydrochloric acid and then water, dried over sodium sulfate filtered and the solvent is evaporated under reduced pressure. The residue is chromatography over silicagel (eluant: n-hexane / acetic acid ethyl-ester 2:1). The title compound is obtained as a colourless foam:

$^1$H-NMR: 1.41 (d, J=7 Hz); 4.34 [q, J=7 Hz, —COCH(CH$_3$)OSi]; 4.75 (m, H-33).

EXAMPLE 20

FK 506-33-glycolate

[Formula I: $R_1$ = a group (c) wherein $R_6$ = OMe, $R_7$ = $R_8R_9$CHCOO— ($R_8$ = OH, $R_9$ = H); $R_2$ = OH, single bond in 23,24 position; $R_3$ = allyl; $R_4$ = OH, single bond in 10,11 position]

[Process variant e)]

To a solution of 300 mg tert-butyldimethylsilyloxymethylcarboxylic acid in 5 ml of dichloromethane are added under stirring at 0° 0.67 ml of oxalyl chloride and one drop of dimethylformamide. The mixture is brought to room temperature and is stirred for 1 hour. The reaction mixture is concentrated under reduced pressure. The residue is taken up in 5 ml of dichloromethane and this solution is added dropwise at 0° to a solution of 600 mg FK 506, 0.28 ml triethylamine and a catalytic quantity of 4-dimethylaminopyridine. After 18 hours at 0° the solution is diluted with acetic acid ethyl ester, successively washed with 0.1 N hydrochloric acid and water, and the organic phase is dried over sodium sulfate, filtered and concentrated under reduced pressure. The residue is taken up in 20 ml of acetonitrile, reacted with 0.5 ml of 40% wt. aqueous hydrofluoric acid and stirred for 20 minutes at room temperature. The mixture is diluted with acetic acid ethyl ester, washed with saturated aqueous sodium hydrogen carbonate solution, dried over sodium sulfate, filtered and concentrated under reduced pressure. The title compound is obtained as a colourless foamy resin from the residue by chromatography over silicagel (eluant: n-hexane / acetic acid ethyl ester):

$^1$H-NMR: 4.13 (s, —COCCH$_2$OH); 4.41 (d, br, J=13 Hz, H-6e); 4.60 (d, br, J=4 Hz, H-2); 4.78 (m, H-33); 5.16 + 5.30-(H-26).

| Example No. | Analogous to Ex. No. | $R_1$ | $R_5$ | $R_6$ | $R_7$ | $R_2$ | Position 23,24 | $R_3$ | $R_4$ | Position 10,11 | Physico-chemical characterization data |
|---|---|---|---|---|---|---|---|---|---|---|---|
| 21 | 17 to 20 | (c) | na | OMe | BOC—NHCH$_2$COO— | OtBDMS | sb | allyl | OH | sb | cfr; NMR* |
| 22 | 17 to 20 | (c) | na | OMe | tBDMS—OCH$_2$COO— | OtBDMS | sb | allyl | OH | sb | cfr; NMR* |
| 23 | 17 to 20 | (c) | na | OMe | BOC—NHCH$_2$COO— | OtBDMS | sb | Et | OH | sb | cfr |
| 24 | 17 to 20 | (c) | na | OMe | tBDMS—OCH$_2$COO— | OtBDMS | sb | Et | OH | sb | cfr; NMR* |
| 25a | 17 to 20 | (c) | na | OMe | BOC—NHCH$_2$COO— | OH | sb | allyl | OH | sb | cfr; NMR* |
| 25b | 17 to 20 | (c) | na | OMe | OH | BOC—NHCH$_2$COO— | sb | allyl | OH | sb | cfr; NMR* |
| 25c | 17 to 20 | (c) | na | OMe | BOC—NHCH$_2$COO— | BOC—NHCH$_2$COO— | sb | allyl | OH | sb | cfr; NMR* |
| 25d | 17,19,20 | (c) | na | OMe | BOC—NHCH$_2$COO— | absent | db | allyl | OH | sb | cfr; |
| 26a | 17 to 20 | (c) | na | OMe | BOC—NHCH$_2$COO— | OH | sb | Et | OH | sb | cfr |
| 26b | 17 to 20 | (c) | na | OMe | OH | BOC—NHCH$_2$COO— | sb | Et | OH | sb | cfr |
| 26c | 17 to 20 | (c) | na | OMe | BOC—NHCH$_2$COO— | BOC—NHCH$_2$COO— | sb | Et | OH | sb | cfr |
| 26d | 17 to 20 | (c) | na | OMe | BOC—NHCH$_2$COO— | absent | db | Et | OH | sb | cfr |
| 27a | 17 to 20 | (c) | na | OMe | NH$_2$COCOO— | OH | sb | allyl | OH | sb | cfr |
| 27b | 17 to 20 | (c) | na | OMe | NH$_2$COCOO— | NH$_2$COCOO— | sb | allyl | OH | sb | cfr; NMR* |
| 27c | 17 to 20 | (c) | na | OMe | NH$_2$COCOO— | absent | db | allyl | OH | sb | cfr |
| 28a | 17 to 20 | (c) | na | OMe | NH$_2$COCOO— | OH | sb | Et | OH | sb | cfr; NMR* |
| 28b | 17 to 20 | (c) | na | OMe | NH$_2$COCOO— | NH$_2$COCOO— | sb | Et | OH | sb | cfr |
| 28c | 17 to 20 | (c) | na | OMe | NH$_2$COCOO— | absent | db | Et | OH | sb | cfr |
| 29 | 17 to 20 | (c) | na | OMe | NH$_2$COCOO— | OtBDMS | sb | Et | OH | sb | cfr; NMR* |

-continued

| Example No. | Analogous to Ex. No. | $R_1$ | $R_5$ | $R_6$ | $R_7$ | $R_2$ | Position 23,24 | $R_3$ | $R_4$ | Position 10,11 | Physico-chemical characterization data |
|---|---|---|---|---|---|---|---|---|---|---|---|
| 30 | 17 to 20 | (c) | na | OMe | NH$_2$COCOO— | OtBDMS | sb | allyl | OH | sb | cfr |
| 31 | 17 to 20 | (c) | na | OMe | p-tolyloxy-thiocarbonyloxy | OH | sb | Et | OH | sb | cfr; NMR* |
| 32 | 17 to 20 | (c) | na | OMe | HOCH$_2$COO— (S) | OH | sb | Et | OH | sb | cfr; NMR* |
| 33 | 17 to 20 | (c) | na | OMe | tBDMS—OCH(CH$_3$)COO— | OH | sb | Et | OH | sb | cfr |
| 34 | 17 to 20 | (c) | na | OMe | iBuoyloxy | OtBDMS | sb | Et | OH | sb | cfr; NMR* |
| 35 | 17 to 20 | (c) | na | OMe | iBuoyloxy | OtBDMS | sb | allyl | OH | sb | cfr |
| 36 | 17 to 20 | (c) | na | OMe | iBuoyloxy | OH | sb | allyl | OH | sb | cfr |
| 37 | 17 to 20 | (c) | na | OMe | iBuoyloxy | OH | sb | Et | OH | sb | cfr; NMR* |
| 38 | 17,18,20 | (c) | na | OMe | tBDMS—OCH(CH$_3$)COO— (S) | OtBDMS | sb | Et | OH | sb | cfr; NMR* |

*$^1$H-NMR: Example 21: mixture of conformers: 4.85(m, H-33); 3.93(s, O=C—CH$_2$—N—); 3.22(m, H-32);
$^1$H-NMR: Example 22: 4.25(s, —COCH$_2$OSi); 4.76(m, H-33);
$^1$H-NMR: Example 24: 4.26(s, —COCH$_2$OSi);
$^1$H-NMR: Example 25a: 5.7(m, H-37); 4.75(dxdxd, J=5Hz, 9Hz and 10Hz, H-33); 3.93(m, N—CH$_2$—); 1.46(s, tBu);
$^1$H-NMR: Example 25b: mixture of conformers: 5.69(m, H-37); 4.52(H-2); 4.44(H-6eq.); 3.87(m, —N—CH$_2$—C=O); 1.46(s, N—BOC);
$^1$H-NMR: Example 25c: 5.7(m, H-37); 4.76(dxdxd, J=5Hz, 8Hz and 10Hz, H-33); 3.93/3.87(m/m, —N—CH$_2$); 1.46(s, tBu);
$^1$H-NMR: Example 27b: about 2:1 mixture of conformers: 7.15-7.0 and 6.1-6.2(b, each 2H, O=C—NH$_2$); 5.28 and 5.42(q/q, J=5 and 5Hz, H-24); 4.84(m, H-33);
$^1$H-NMR: Example 28a: mixture of conformers: 7.01 and 5.98(—CONH$_2$); 5.35(d, J=1Hz, H-26); 4.85(m, H-33); 4.61(db, J=3Hz, H-2); 4.44(db, J=13Hz, H-6eq.);
$^1$H-NMR: Example 29: mixture of conformers: 7.03 and 6.12(CONH$_2$); 4.85(m, H-33); 4.45(H-2); 4.42(H-6eq.); 0.88(s, tBu); 0.04(s, Si—CH$_3$);
$^1$H-NMR: Example 31: mixture of conformers: 7.22/7.02(AA'BB'-syst., ar-H); 5.35(d, J=1Hz, H-26); 5.18(m, H-33); 4.63(db, J=4Hz, H-2); 4.45(db, J=13Hz, H-6eq.); 2.37(s, ar-CH$_3$);
$^1$H-NMR: Example 32: 4.13(s, —COCH$_2$OH); 4.40(d, br, J=13Hz, H-6e); 4.58(d, br, J=4Hz, H-2); 4.78(m, H-33); 5.17 + 5.30(H-26);
$^1$H-NMR: Example 34: 4.69(m, H-33); 2.55(septet, J=7Hz, O=C—CH(CH$_3$)$_2$]; 1.17[d, J=7Hz, C(CH$_3$)$_2$];
$^1$H-NMR: Example 37: 4.68(dxdxd, J=5Hz, 10Hz and 11Hz, H-33); 2.55[septet, J=7Hz, O=C—CH(CH$_3$)$_2$]; 1.17[d, J=7Hz, C(CH$_3$)$_2$]; Minor component: 1.23(d, J=7Hz; 4.30[dq, J$_1$=5Hz, J$_2$=7Hz, —COCH(CH$_3$)OH]; 4.78(ddd, J$_1$=5Hz, J$_2$=9Hz, J$_3$=11Hz, H-33); 5.20(H-26);
$^1$H-NMR: Example 38: see Example 19.

EXAMPLE 39

24-tert-Butyldimethylsilyloxy-33-aminooxalyloxy-FK 506

[Formula I: $R_1$ = a group (c) wherein $R_6$ = OMe, $R_7$ = aminooxalyloxy; $R_2$ = OtBDMS, single bond in 23,24 position; $R_3$ = allyl; $R_4$ = OH, single bond in 10,11 position].

[Process variant f), treatment with oxalyl chloride and ammonia]

A solution of 24,33-bis-(tert-butyldimethylsilyloxy)-FK 506 in 70 ml of acetonitrile is reacted at 0° to 5° with 1 ml of oxatyl chloride and stirred at 0° to 5° for 40 minutes. Thee reaction mixture is stirred with a mixture of acetic acid ethyl ester and satured aqueous ammonia solution, any precipitate formed is sucked off, the phases are separated, the organic phase is successively washed with 1 N hydrochloric acid and then water, dried over sodium sulfate, filtered, and concentrated under reduced pressure. From the residue the-title compound is obtained as a colourless foamy resin following column chromatography over silicagel (eluant: n-hexane/ acetic acid ethyl ester 1:1):

$^1$H-NMR: about 2:1 mixture of conformers: 7.04 and 6.17 (b, each 1 H, H$_2$NC-O); 4.86 (m, H-33).

EXAMPLE 43

24-Methoxy-33-tert-butyldimethylsilyloxy-FK 506

[Formula I: $R_1$ = a group (c) wherein $R_6$ = OMe, $R_7$ = OtBDMS; $R_2$ = OMe, single bond in 23,24 position; $R_3$ = allyl; $R_4$ = OH, single bond in 10,11 position]

[Process variant g), methylation]

1 g 33-tert-butyldimethylsilyloxy-FK 506 is dissolved into a mixture of 50 ml of dichloromethane and 0.04 ml of borotrifluoride etherate previously cooled to 0° to 5°. A solution of 20 ml of an approximately 1 N solution of diazomethane in methylene chloride is then added dropwise in such a manner that the yellow coloration of the solution which initially forms persists for as shortly as possible. The reaction mixture is diluted with acetic acid ethyl ester, successively washed with saturated aqueous sodium hydrogen .carbonate solution and water, dried over sodium sulfate, filtered and the solvent is removed under reduced pressure. The title compound is obtained as a colourless foamy resin from the residue following column chromatographic purification over silicagel (eluant: acetic acid ethyl ester / n-hexane):

$^1$H-NMR: about 3:1 mixture of conformers: main conformer: 5.25 (d, J=8 Hz, H-29); 5.17 (d, J=7 Hz, H-26); 4.79 (d, J=10 Hz, H-20); 3.82 (dxd, J-9 Hz and 1.5 Hz, H-14); 3.42, 3.40, 3.33 and 3.24 (4xs, OCH$_3$); 2.68 (dxd, J=13 Hz and 8 Hz, H-23 ); minor conformer: 3.90 (dxd, J=9/2,5 Hz, H-14);

| Example No. | Analogous to Ex. No. | $R_1$ | $R_5$ | $R_6$ | $R_7$ | $R_2$ | Position 23,24 | $R_3$ | $R_4$ | Position 10,11 | Physicochemical characterization data |
|---|---|---|---|---|---|---|---|---|---|---|---|
| 40 | 39[1)] | (c) | na | OMe | NH$_2$COCOO— | NH$_2$COCOO— | sb | allyl | OH | sb | cfr; NMR* |
| 41 | 39,40 | (c) | na | OMe | NH$_2$COCOO— | OtBDMS | sb | Et | OH | sb | cfr; NMR* |
| 42 | 39,40 | (c) | na | OMe | NH$_2$COCOO— | NH$_2$COCOO— | sb | Et | OH | sb | cfr |

[1)]Stirring is effected for 1 hour at room temperature; column chromatography is effected using an eluant gradient of 3:1 to 1:3;
*$^1$H-NMR:
Example 40: see Example 27b;
Example 41: see Example 29.

| Example No. | Analogous to Ex. No. | $R_1$ | $R_5$ | $R_6$ | $R_7$ | $R_2$ | Position 23,24 | $R_3$ | $R_4$ | Position 10,11 | Physicochemical characterization data |
|---|---|---|---|---|---|---|---|---|---|---|---|
| 44 | 43[1)] | (c) | na | OMe | OMe | OtBDMS | sb | allyl | OH | sb | cfr; NMR* |

*$^1$H-NMR: about 2:1 mixture of conformers:
main conformer: 5.22(d, J=7Hz, H-26); 4.84(d, J=10Hz, H-20); 4.07(m, H-24); 3.80(dxd, J=9Hz and 1.5Hz, H-14); 3.45, 3.44, 3.40 and 3.32(4xs; OCH$_3$); 2.78(dxd, J=15Hz and 7.5Hz, H-23); 0.87(tBu);
minor conformer: 4.26(m, H-24); 3.94(dxd, J=9Hz and 2.5Hz, H-14); 0.86(tBu);
[1)]Starting from 24-tert-butyldimethylsilyloxy-FK 506.

EXAMPLE 45

24-tert-Butyldimethylsilyloxy-33-oxo-FR 520

[Formula I: $R_1$ = a group (c) wherein $R_6$ = OMe, $R_7$ = oxo; $R_2$ = OtBDMS, single bond in 23,24 position; $R_3$ = Et; $R_4$ = OH, single bond in 10,11 position]

[Process variant h), oxidation]

2 g 24-tert-butyldimethylsilyloxy-FR 520 and 1 g N-methylmorpholin-N-oxide are dissolved in 100 ml of methylene chloride, reacted with 5 g molecular sieve (Molsieb 4A) and the mixture is stirred for 15 minutes at room temperature. 0.15 g tetrapropylammonium perruthenate is added and stirring is continued for 3 more hours at room temperature. The mixture is concentrated, The residue is taken up in acetic acid ethyl ester and the solution successively washed with saturated aqueous sodium hydrogen sulfite solution, saturated aqueous sodium chloride and saturated aqueous copper sulfate solution and the organic phase is dried over sodium sulfate; filtered and concentrated under reduced pressure. The title compound is obtained from the residue following column chromatography over silicagel (eluant: n-hexane / acetic acid ethyl ester).

EXAMPLE 47

24-Oxo-FK 506

[Formula I: $R_1$ = a group (c) wherein $R_6$ = OMe, $R_7$ = OH; $R_2$ = oxo, single bond in 23,24 position; $R_3$ = allyl; $R_4$ = OH, single bond in 10,11 position]

[Process variant deprotection]

3.6 g 24-oxo-33-tert-butyldimethylsilyloxy-FK506 (compound of Example 16b) is dissolved at room temperature into a mixture of 110 ml of acetonitrile and 3 ml of 40% wt. aqueous hydrofluoric acid and the mixture is stirred at room temperature for 45 minutes. The reaction mixture is diluted with acetic acid ethyl ester, washed successively with saturated aqueous sodium bicarbonate solution and then water, dried over sodium sulfate, filtered and concentrated under reduced pressure. The title compound is obtained as a colourless foamy resin following chromatographic purification of the residue over silicagel (eluant: acetic acid ethyl ester / n-hexane 3:2):

$^1$H-NMR: about 1:1 mixture of conformers: 5.80 and 5.60 (s, H-23); 3.44, 3.41, 3.39, 3.38 and 2×3.275 (OCH$_3$):

| Example No. | Analogous to Ex. No. | $R_1$ | $R_5$ | $R_6$ | $R_7$ | $R_2$ | Position 23,24 | $R_3$ | $R_4$ | Position 10,11 | Physicochemical characterization data |
|---|---|---|---|---|---|---|---|---|---|---|---|
| 46 | 45[1)] | (c) | na | OMe | OtBDMS | oxo | sb | Et | OH | sb | cfr |
| 46a | 45[2)] | (c) | na | OMe | oxo | OtBDMS | sb | allyl | OH | sb | cfr; NMR* |
| 46b | 45 | (c) | na | OMe | OtBDMS | oxo | sb | allyl | OH | sb | cfr; NMR* |

*Example 46a: $^{13}$C-NMR: see Example 15a;
Example 46b: $^1$H-NMR and $^{13}$C-NMR: see Example 16b;
[1)]Starting from 33-tert-butyldimethylsilyloxy-FR 520 (DOS 39 38 754);
[2)]Starting from 24-tert-butyldimethylsilyloxy-FK 506;
[3)]Starting from 33-tert-butyldimethylsilyloxy-FK 506;

| Example No. | Analogous to Ex. No. | $R_1$ | $R_5$ | $R_6$ | $R_7$ | $R_2$ | Position 23,24 | $R_3$ | $R_4$ | Position 10,11 | Physicochemical characterization data |
|---|---|---|---|---|---|---|---|---|---|---|---|
| 48 | 47[1)] | (c) | na | OMe | NH$_2$CH$_2$COO— | OH | sb | allyl | OH | sb | cfr; NMR* |
| 49 | 47[2)] | (c) | na | OMe | NH$_2$CH$_2$COO— | absent | db | allyl | OH | sb | cfr; NMR* |
| 50 | 47[3)] | (c) | na | OMe | OH | oxo | sb | Et | OH | sb | cfr; NMR* |
| 51 | 47[4)] | (c) | na | OMe | NH$_2$CH$_2$COO— | OH | sb | Et | OH | sb | cfr; NMR* |
| 52 | 47[5)] | (c) | na | OMe | NH$_2$CH$_2$COO— | absent | db | Et | OH | sb | cfr |
| 53 | 47[6)] | (c) | na | OMe | HOCH$_2$COO— | OH | sb | allyl | OH | sb | cfr; NMR* |
| 54 | 47[7)] | (c) | na | OMe | HOCH$_2$COO— | OH | sb | Et | OH | sb | cfr; NMR* |
| 55 | 47[8)] | (c) | na | OMe | HOCH(CH$_3$)COO— (S) | OH | sb | Et | OH | sb | cfr; NMR* |
| 56 | 47[9)] | (c) | na | OMe | OH | NH$_2$CH$_2$COO— | sb | Et | OH | sb | cfr |
| 57 | 47[10)] | (c) | na | OMe | NH$_2$CH$_2$COO— | NH$_2$CH$_2$COO— | sb | Et | OH | sb | cfr |
| 58 | 47[11)] | (c) | na | OMe | NH$_2$CH$_2$COO— | NH$_2$CH$_2$COO— | sb | allyl | OH | sb | cfr |
| 59 | 47[12)] | (c) | na | OMe | OH | NH$_2$CH$_2$COO— | sb | allyl | OH | sb | cfr |
| 60 | 47[13)] | (c) | na | OMe | NH$_2$CH$_2$COO— | OH | sb | allyl | OH | sb | cfr; NMR* |
| 61 | 47[14)] | (c) | na | OMe | NH$_2$CH$_2$COO— | OH | sb | Et | OH | sb | cfr; NMR* |
| 62 | 47[15)] | (c) | na | OMe | iBuoyloxy | OH | sb | Et | OH | sb | cfr; NMR* |
| 63 | 47[16)] | (c) | na | OMe | iBuoyloxy | OH | sb | allyl | OH | sb | cfr |
| 64 | 47[17)] | (a) | I | OMe | na | OH | sb | Et | OH | sb | cfr;** |
| 65a | 47[18)] | (a) | Cl | OMe | na | OH | sb | allyl | OH | sb | cfr; NMR* |
| 65b | 47[18)] | (a) | Cl | OMe | na | OH | sb | allyl | absent | db | cfr |
| 66a | 47[19)] | (a) | Cl | OMe | na | OH | sb | Et | OH | sb | cfr; NMR* |
| 66b | 47[19)] | (a) | Cl | OMe | na | OH | sb | Et | absent | db | cfr; NMR* |

-continued

| Example No. | Analogous to Ex. No. | R₁ | R₅ | R₆ | R₇ | R₂ | Position 23,24 | R₃ | R₄ | Position 10,11 | Physicochemical characterization data |
|---|---|---|---|---|---|---|---|---|---|---|---|
| 67a | 47[20)] | (a) | Br | OMe | na | OH | sb | Et | OH | sb | cfr; NMR* |
| 67b | 47[20)] | (a) | Br | OMe | na | OH | sb | Et | absent | db | cfr |
| 68a | 47[21)] | (a) | N₃ | OMe | na | OH | sb | allyl | OH | sb | cfr; NMR* |
| 68b | 47[21)] | (a) | N₃ | OMe | na | OH | sb | allyl | absent | db | cfr; NMR* |
| 69a | 47[22)] | (a) | Br | OMe | na | OH | sb | allyl | OH | sb | cfr |
| 69b | 47[22)] | (a) | Br | OMe | na | OH | sb | allyl | absent | db | cfr |
| 70a | 47[23)] | (a) | N₃ | OMe | na | OH | sb | Et | OH | sb | cfr; NMR* |
| 70b | 47[23)] | (a) | N₃ | OMe | na | OH | sb | Et | absent | db | cfr |

[1)] Starting from the compound of Example 25a;
[2)] Starting from the compound of Example 25d;
[3)] Starting from the compound of Example 46 (=16d);
[4)] Starting from the compound of Example 23;
[5)] Starting from the compound of Example 26d;
[6)] Starting from the compound of Example 22;
[7)] Starting from the compound of Example 24;
[8)] Starting from the compound of Example 19 or of Example 33;
[9)] Starting from the compound of Example 26b;
[10)] Starting from the compound of Example 26c;
[11)] Starting from the compound of Example 25c;
[12)] Starting from the compound of Example 25b;
[13)] Starting from the compound of Example 25a;
[14)] Starting from the compound of Example 26a;
[15)] Starting from the compound of Example 34;
[16)] Starting from the compound of Example 35;
[17)] Starting from the compound of Example 6a;
[18)] Starting from the compound of Example 1;
[19)] Starting from the compound of Example 3;
[20)] Starting from the compound of Example 4;
[21)] Starting from the compound of Example 2;
[22)] Starting from the compound of Example 5;
[23)] Starting from the compound of Example 6;
*NMR:
Example 48: ¹H-NMR: about 2:1 mixture of conformers: 5.33 and 5.20(d/d, J=1Hz and 1Hz, H-26); 4.84(dxdxd, J=5Hz, 9.5Hz and 11Hz, H-33); 3.44(s, 2H, O=C—CH₂—N—); 3.22(dxdxd, J=5Hz, 9.5Hz and 11Hz, H-32);
Example 49: ¹H-NMR: see Example 18;
Example 50: ¹H-NMR: mixture of conformers: 5.8 and 5.6(s/s, H-23); 5.69(H-26); 4.38(d, J=13Hz, H-6e); 4.19(t, H-2); 3.80(dxd, J=9Hz and 2Hz, H-14);
Example 51: ¹H-NMR: about 2:1 mixture of conformers: 5.34(d, J=2Hz, H-26); 4.75(dxdxd, J=5Hz, 9Hz and 10Hz, H-33); 4.61(db, J=4Hz, H-2); 4.44(db, J=13Hz, H-6e); 3.45(s, —CH₂—N);
Example 53: ¹H-NMR: see Example 20;
Example 54: ¹H-NMR: see Example 32;
Example 55: ¹H-NMR: mixture of conformers: main conformer: 1.23(d, J=7Hz); 4.30[dq, J₁=5Hz, J₂=7Hz, —COCH(CH₃)OH]; 4.44(d, br, J=13Hz, H-6e); 4.61(d, br, J=4Hz); 4.78(ddd, J₁=5Hz, J₂=5Hz, J₃=11Hz, H-33); 5.34(H-26);
Example 60: ¹H-NMR: see Example 48;
Example 61: ¹H-NMR: see Example 51;
Example 62: ¹H-NMR: see Example 37;
Example 65a:
¹H-NMR 4.59(m, H-33);
¹³C-NMR: about 2:3 mixture of conformers: main conformer: 59.1(C-33; 79.2(C-32); 97.5(C-10); 116.4(C-38); 123.0(C-20); 135.6(C-37); 138.4(C-19); 164.6(C-8); 168.9(C-1); 196.4(C-9); 209.4(C-22);
Example 66a: ¹H-NMR: 4.56(m, H-33);
Example 66b:
¹H-NMR: 2.09(s, 11-CH₃); 4.5(bm, H-33);
¹³C-NMR: about 2:1 mixture of conformers:
main conformer: 56.2(C-33); 80.6(C-32); 116.4(C-38); 122.9(C-20); 124.8(C-11); 129.5(C-29); 131.9(C-28): 135.8(C-37); 140.0(C-19); 142.9(C-10); 166.7(C-8); 168.7(C-1); 188.0(C-9); 212.4(C-22);
minor conformer: 56.1(C-33); 80.6(C-32); 116.5(C-38); 123.6(C-20); 126.4(C-11); 128.5(C-29); 131.8(C-28); 135.6(C-37); 137.4(C-19); 144.1(C-10); 166.5(C-8); 169.5(C-1); 184.8(C-9); 213.3(C-22);
Example 67a: ¹H-NMR: 4.44(d, J=13Hz, H-6eq.); 4.60(d, J=4Hz, H-2); 4.70(sb, H-33);
Example 68a: ¹H-NMR: 4.07(m, w₁=8Hz, H-33);
Example 68b: ¹H-NMR: about 2:1 mixture of conformers: 4.06(m, H-33); 2.09 and 1.94(2s, 11-CH₃);
Example 70a: ¹H-NMR: about 5:4 mixture of conformers: 5.60 resp. 5.79(s resp. s, H-23); 5.70 resp. 5.66(d, J=3Hz resp. d, J=3Hz, H-26); 4.38(d, J=13Hz, H-6e); 4.15(t, H-2); 3.80(dxd, J=9Hz and 2Hz, H-14).
**Iodine analysis: theor.: 14.06%; found: 13.57%.
The compounds of Examples 10a, 11a, 12, 13, 27a and 28a may be prepared in analogous manner according to process variant deprotection.

EXAMPLE 71

24-tert-Butyldimethylsilyloxy-29-des-(4-hydroxy-3-methylcyclohexyl)-29-(3-formylcyclopentyl)-FR 520

[Formula I: R₁ = a group (d); R₂ = OtBDMS, single bond in 23,24 position; R₃ = Et; R₄ = OH, single bond in 10,11 position]

[Process variant protection]

A solution of 1.2 g 29-des-(4-hydroxy-3-methylcyclohexyl)-29-(3-formylcyclopentyl)-FR 520 (compound of Example 12), 1.5 g tert-butyldimethylsilyl chloride and 0.8 g imidazole in 20 ml of dry dimethylformamide is stirred for 15 hours at room temperature and thereafter partitioned between 1 N hydrochloric acid solution and acetic acid ethyl ester. The organic phase is separated, washed with saturated aqueous sodium chloride solution, dried over sodium sulfate, filtered and concentrated under reduced pressure. The title compound is obtained from the residue as a colourless foamy resin following column chromatography over silicagel (eluant: n-hexane / acetic acid ethyl ester):

¹H-NMR: mixture of rotamers: 9.65 (d, J = 2 Hz, CHO); 5.39 (d, J = 9 Hz, H-29); 5.01 (d, J = 7.5 Hz, H-26); 4.81 (d, J = 10 Hz, H-20); 3.82 (dxd, J = 9/2 Hz, H-24).

The compounds of Examples 1 to 9, 16a to 16d, 19, 21 to 26d, 29, 30, 34, 35, 38, 39, 41 and 43 to 46b may be prepared in analogous manner according to process variant protection.

The compounds of the invention possess pharmacological activity. They are useful as pharmaceuticals.

In particular they possess antiinflammatory, and immunosuppressant and antiproliferative activity.

Antiinflammatory activity may e.g. be determined in the following test methods:

1. Oxazolone allergic contact dermatitis in the mouse in vivo upon topical application: the test method is as described in F.M. Dietrich and R. Hess, Int. Arch. Allergy 38 (1970) 246–259.

The compounds elicit in this test an activity between about 15% and about 68% upon topical administration at a concentration of about 0.01%.

2. DNFB allergy (swine): the test method is as described in e.g. EP 315978.

Topical application of a 1.2% formulation of the compounds repeated twice results in from about 36% to about 40% inhibition of the inflammatory reaction.

Immunosuppressant and antiproliferative activity may e.g. be determined in the following test methods:

1. Proliferative response of lymphocytes to allogen stimulation in the mixed lymphocyte reaction (MLR) in vitro: T. Meo, "The MLR in the Mouse", Immunological Methods, L. Lefkovits and B. Pernis, Eds., Academic Press, N.Y. (1979), 227–239.

The compounds elicit in this test ($IC_{50}$) suppression of mixed lymphocytes at a dosage of from about $< 0.0008$ $\mu g/ml$ to about 0.09 $\mu g/ml$.

2. Inhibition of the primary humoral immune response to sheep erythrocytes in vitro: the test method is as described in R.I. Mishell and R.W. Dutton, Science 153 (1966) 1004–1006; R.I. Mishell and R.W. Dutton, J. Exp. Med. 126 (1967) 423–442.

The compounds are active in this test with an $IC_{50}$ of from about 0.0024 $\mu g/ml$ to about 0.32 $\mu g/ml$.

3. Inhibition of proliferation of human keratinocytes: the test method is as described in e.g. EP 315978.

The compounds are active in this test at concentrations of from about 1 $\mu g/ml$ to about 10 $\mu g/ml$ resulting in an inhibition of from about 30% to about 90%.

The compound of Example 12 is the preferred compound as an immunosuppressant agent. It has, for example, been determined that in the above mixed lymphocyte reaction test this compound has in $IC_{50}$ of less than 0.0008 $\mu g/ml$, as compared to 0.002 $\mu g/ml$ for cyclosporin A. It is, therefore, indicated that for this indication the compound of Example 12 may be administered to larger mammals, for example humans, by similar modes of administration at similar or lower dosages than conventionally employed with cyclosporin A.

The compounds of the invention in free form and where such forms exist in pharmaceutically acceptable salt form are therefore useful as antiinflammatory and as immunosuppressant and antiproliferative agents for the prevention and treatment of inflammatory conditions and of conditions requiring immunosuppression, such as a) the prevention and treatment of
   resistance in situations of organ or tissue transplantation, e.g. of heart, kidney, liver, bone marrow and skin,
   graft-versus-host disease, such as following bone marrow grafts,
   autoimmune diseases such as rheumatoid arthritis, systemic Lupus erythematosus, Hashimoto's thyroidis, multiple sclerosis, Myasthenia gravis, diabetes type I and uveitis,
   cutaneous manifestations of immunologically-mediated illnesses;

b) the treatment of inflammatory and hyperproliferative skin diseases, such as psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus and acne; and c) Alopecia arcata.

The compounds may be administered systemically or topically.

For these indications the appropriate dosage will, of course, vary depending upon, for example, the host, the mode of administration and the nature and severity of the condition being treated. However, in general, satisfactory results are indicated to be obtained systemically at daily dosages of from about 0.15 mg/kg to about 1.5 mg/kg animal body weight. An indicated daily dosage in the larger mammal is in the range from about 0.01 mg to about 100 mg, conveniently administered, for example, in divided doses up to four times a day or in retard form.

For topical use satisfactory results are obtained with local administration of a 1–3% concentration of active substance several times daily, e.g. 2 to 5 times daily. Examples of indicated galenical forms are lotions, gels and creams.

The compounds of the invention may be administered by any conventional route, in particular enterally, e.g. orally, e.g. in the form of tablets or capsules, or topically, e.g. in the form of lotions, gels or creams.

Pharmaceutical compositions comprising a compound of the invention in association with at least one pharmaceutical acceptable carrier or diluent may be manufactured in conventional manner by mixing with a pharmaceutically acceptable carrier or diluent. Unit dosage forms contain, for example, from about 0.0025 mg to about 50 mg of active substance.

Topical administration is e.g. to the skin. A further form of topical administration is to the eye, for the treatment of immune-mediated conditions of the eye, such as: auto-immune diseases, e.g. uveitis, keratoplasty and chronic karatiris; allergic conditions, e.g. vernal conjunctivitis; inflammatory conditions and corneal transplants, by the topical administration to the eye surface of a compound of the invention in a pharmaceutically acceptable ophthalmic vehicle.

The ophthalmic vehicle is such that the compound is maintained in contact with the ocular surface for-a sufficient time period to allow the compound to penetrate the corneal and internal regions of the eye, e.g. the anterior chamber, posterior chamber, vitreous body, aqueous humor, vitreous humor, cornea, iris/ciliary, lens, choroid/retina and sclera.

The pharmaceutically acceptable ophthalmic vehicle may be e.g. an ointment, vegetable oil, or an encapsulating material.

Whilst the antiinflammatory and immunosuppressant and antiproliferative activity is the main activity of the compounds of the invention they also possesses some degree of activity in increasing sensitivity to, or in increasing the efficacy of, chemotherapeutic drug therapy.

This activity may e.g. be determined according to the test methods described in EP 360760.

The compounds of the invention are therefore useful in reversing chemotherapeutic drug resistance of varying types, e.g. acquired or innate, or in increasing sensitivity to administered drug therapy, e.g. as a means of reducing regular chemotherapeutic dosage levels, for example in the case of anti-neoplastic or cytostatic drug therapy, as a means of decreasing overall drug toxicity and, more especially, as a means of reversing or reducing resistance, including both inherent and acquired resistance, to chemotherapy.

Preferred in the above indications are the following compounds of the invention:

29-des-(4-hydroxy-3-methoxycyclohexyl)-29-(3-formylcyclopentyl)-FR 520 (compound of Example 12);
33-aminooxalyloxy-FR 520 (compound of Example 28a);
FR 520-33-glycolate (compound of Examples 32 and 54);
33-isobutanoyloxy-FR 520 (compound of Examples 37 and 62); and
33-epi-33-chloro-FR 520 (compound of Example 66a).

We claim:

1. A compound of formula

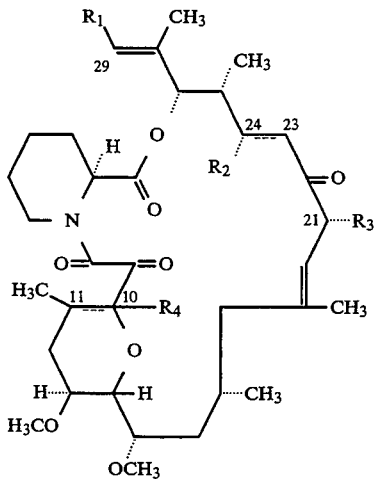

wherein
R₁ is a group (d) of formula

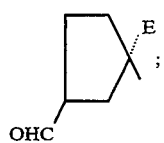

R₂ is oxo and there is a single bond n 23,24 position; hydroxy or hydroxy protected by a hydroxy protecting group selected from formyl, tert-butoxycarbonyl, and trialkylsilyl and there is a single or a double bond in 23,24 position; or absent and there is a double bond in 23,24 position; and
R₄ is hydroxy and there is a single bond in 10,11 position;
R₃ is methyl, ethyl, n-propyl, or allyl;
in free form or, where such forms exist, in salt form.

2. A compound according to claim 1, wherein
R₂ is hydroxy or hydroxy protected by a hydroxy protecting group selected from formyl, tert-butoxycarbonyl, and tert-butyldimethyl-silyl and there is a single bond in 23,24 position; or absent and there is a double bond in 23,24 position;
R₄ is hydroxy and there is a single bond in 10,11 position; and
R₃ is as defined in claim 1;
in free form or, where such forms exist, in salt form.

3. The compound of claim 1 in which R₄ is OH and position 10,11 is a single bond and R₂, R₃, and position 23,24 are a) OH, allyl, and single bond; or b) absent, Et, and double bond.

4. A compound according to claim 1 in which
R₂ is hydroxy or hydroxy protected by tert-butyldimethylsilyloxy and there is a single bond in 23,24 position; or absent an there is a double bond in 23,24 position;
R₄ is hydroxy and there is a single bond in 10,11 position; and
R₃ is ethyl or allyl;
in free form or, where such forms exist, in salt form.

5. The compound according to claim 1 which is 29-des-(4-hydroxy-3-methoxycyclohexyl)-29-(3-formylcyclopentyl) -FR 520.

6. A pharmaceutical composition comprising a therapeutically effective amount of a compound according to claim 1 in free base form or, where such forms exist, in pharmaceutically acceptable salt form, together with a pharmaceutically acceptable carrier therefor.

7. A method of treating inflammation or inducing immunosuppression or inhibiting cell proliferation or reversing chemotherapeutic drug resistance, which comprises administering to a patient in need of said treatment a therapeutically effective amount of a compound according to claim 1 in free base form or, where such forms exist, in pharmaceutically acceptable salt form.

8. A compound of formula I

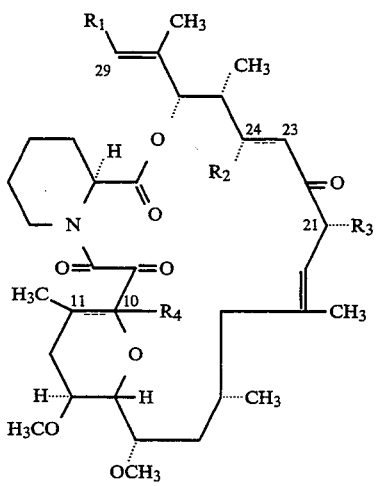

wherein
R₁ is a group (b)

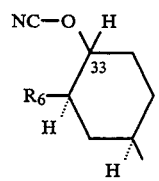

wherein R₆ is hydroxy or methoxy;
R₂ is oxo and there is a single bond in 23,24 position; hydroxy or hydroxy protected by a hydroxy protecting group selected from formyl, tert-butoxycarbonyl, and trialkylsilyl and there is a single or a double bond 23,24 position; or absent and there is a double bond in 23,24 position;

$R_4$ is hydroxy and there is a single bond in 10,11 position; and $R_3$ is methyl, ethyl, n-propyl, or allyl;

in free form or, where such forms exist, in salt form.

9. A compound according to claim 8 wherein $R_6$ is methoxy;

$R_2$ is hydroxy or hydroxy protected by a hydroxy protecting group selected from formyl, tert-butoxycarbonyl, and tert-butyldimethyl silyl silyloxy and there is a single bond in 23,24 position; or absent and there is a double bond in 23,24 position;

$R_4$ is hydroxy and there is a single bond in 10,11 position; and $R_3$ is as defined in claim 8, in free form or, where such forms exist, in salt form.

10. The compound of claim 8 in which $R_4$ is OH, $R_6$ is OMe, and position 10,11 is a single bond and $R_2$, $R_3$, and position 23,24 are a) OtBDMS, Et and single bond; b) OtBDMS, allyl, and single bond; c) OH, Et, and single bond; d) absent, Et and double bond; e) OH, allyl, and single bond; or f) absent, allyl, and double bond.

11. A compound according to claim 8 in which $R_6$ is methoxy;

$R_2$ is hydroxy protected by tert-butyldimethylsilyloxy and there is a single bond in 23,24 position; or absent and there is a double bond in 23,24 position;

$R_4$ is hydroxy and there is a single bond in 10,11 position; and $R_3$ is ethyl or allyl;

in free form or, where such forms exist, in salt form.

12. A pharmaceutical composition comprising a therapeutically effective amount of a compound according to claim 8 in free form or, where such forms exist, in pharmaceutically acceptable salt form, together with a pharmaceutically acceptable carrier or diluent.

13. A method of treating inflammation or inducing immunosuppression or inhibiting cell proliferation or reversing chemotherapeutic drug resistance, which comprises administering to a patient in need of said treatment a therapeutically effective amount of a compound according to claim 8 in free base form or, where such forms exist, in pharmaceutically acceptable salt form.

* * * * *